United States Patent [19]

Zweymüller

[11] 4,404,693
[45] Sep. 20, 1983

[54] SHANK FOR A HIP JOINT PROSTHESIS

[75] Inventor: Karl Zweymüller, Vienna, Austria

[73] Assignee: Sulzer Brothers Limited, Winterthur, Switzerland

[21] Appl. No.: 221,255

[22] Filed: Dec. 30, 1980

[30] Foreign Application Priority Data

Jan. 14, 1980 [CH] Switzerland .......................... 257/80

[51] Int. Cl.³ .............................................. A61F 1/04
[52] U.S. Cl. .................................... 3/1.913; 128/92 C
[58] Field of Search ..................... 3/1.91, 1.912, 1.913; 128/92 C, 92 CA

[56] References Cited

U.S. PATENT DOCUMENTS 3,623,164 11/1971 Bokros ............................ 128/92 CA
3,744,061 7/1973 Frost ..................................... 3/1.912
3,965,490 6/1976 Murray et al. .................. 128/92 CA

FOREIGN PATENT DOCUMENTS 2627569 12/1977 Fed. Rep. of Germany ....... 3/1.913
482509 7/1953 Italy ................................. 128/92 CA
1409054 11/1975 United Kingdom ................. 3/1.913

Primary Examiner—Richard J. Apley
Assistant Examiner—David J. Isabella
Attorney, Agent, or Firm—Kenyon & Kenyon

[57] ABSTRACT

The shank blade widens conically to all sides from a distal end to a point between ⅔ and ¾ of the height of the shank. The upper portion of the blade is thinner and tapers to the collar. The shank avoids the so called "closure (final rotation" which is caused by too small a space for the shank blade in the neck of a femur bone. The shank blade has a generally rectangular cross-section with rounded corners to fit against the cortical bone tissue and has a trochanter wing to improve transmission of torque from the surrounding musculature to the hip joint.

12 Claims, 6 Drawing Figures

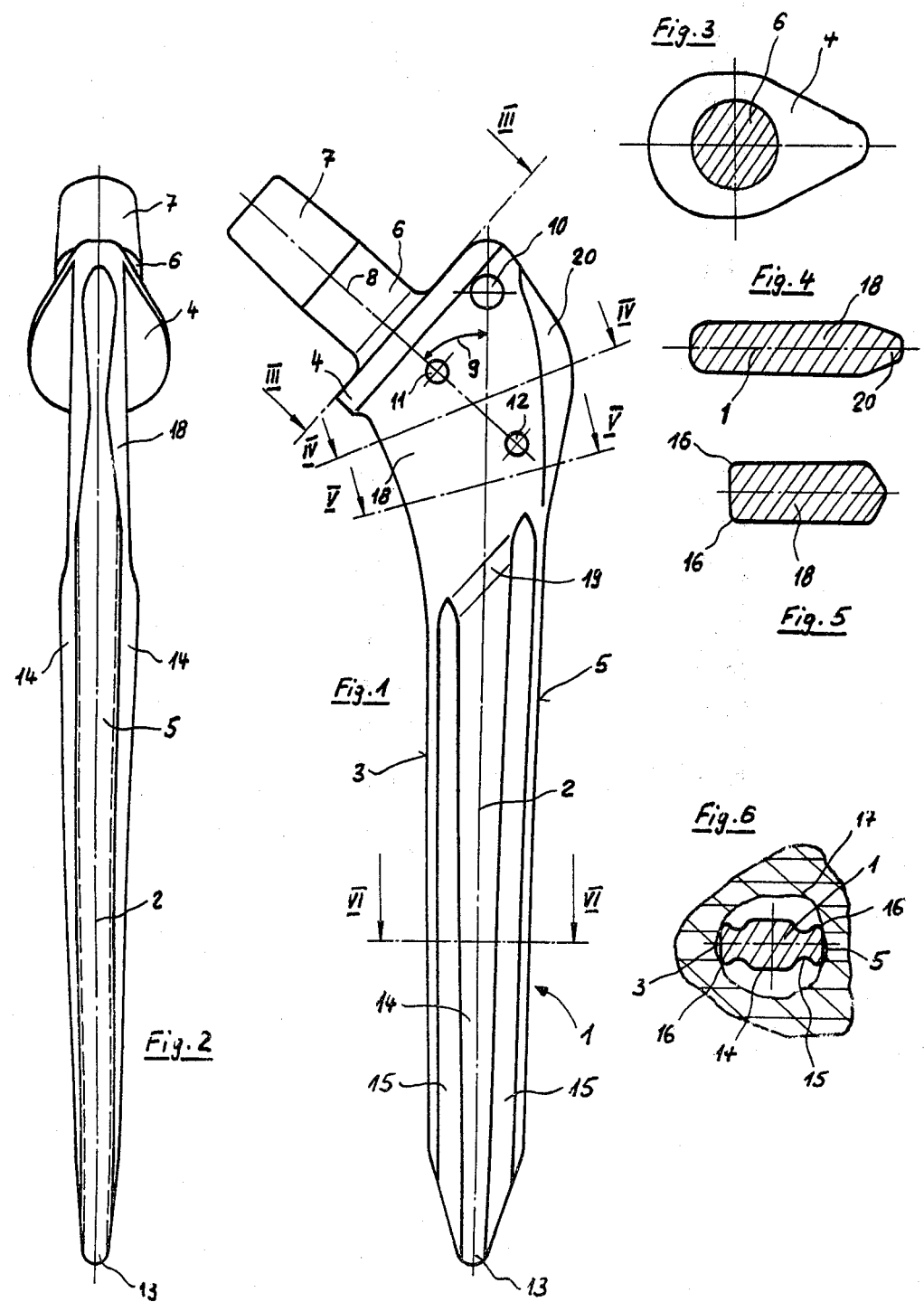

SHANK FOR A HIP JOINT PROSTHESIS

This invention relates to a shank for a hip joint prosthesis. More particularly, this invention relates to a shank having a blade for anchoring a hip joint prosthesis in a femur.

Heretofore, various types of blade-type shanks have been known for anchoring hip joint prosthesis in femurs. In some case, in order to achieve a clamping in a femur bone, for example as described in DE-OS No. 27 46 664, with little or no cement for anchoring, the shanks have been constructed with a blade which first widens conically to all sides from a distal free end in the direction of the longitudinal median axis up to a collar type projection which separates the blade sides from a neck of the prosthesis. In addition, the medial narrow side of the blade changes over from the conical shape to a steadily curved bend which terminates at the collar type projection. In this case, a certain minimum thickness of the shank blade is necessary.

Implantation of the shank portion of a hip joint prosthesis normally follows after resection of the hip head as well as a contiguous portion of the neck of the femur. With a complete insertion or driving in of the conventional prosthesis shank, a so called "closure (or final) rotation" of the shank in the femur bone frequently occurs. This is due to the multiple bends of the proximal femur end as a straight or even slightly curved object is deflected from the wall of the thigh bone. The shank thus follows the path of least resistance unless the most of or all of the femur neck is removed.

Even if the loss of bone substance is acceptable, with a blade type shank, the resection plane at the femur neck cannot be placed too low in order to create the necessary path. In fact, the blade sides should, in the case of a blade type shank, extend parallel to the transverse axis of the knee joint in order to permit a standard implantation and to insure an ideal position of the head of the shank prosthesis in a likewise replaced pelvis. Too low a resection cut causes the resection surface of the femur neck, which is normally approximately of rectangular form, to no longer be parallel to the knee joint axis along the longitudinal axis. Thus, the implantation of the shank is made difficult. But for the blade sides of the prosthesis to be placed parallel to the knee joint axis, the resection must be carried out at midheight of the femur neck.

Accordingly, it is an object of the invention to avoid a "closure rotation" when inserting a hip joint prosthesis.

It is another object of the invention to avoid a "closure rotation" without having to place a resection plane on the femur neck too low.

It is another object of the invention to provide a blade-type shank for a hip joint prosthesis which can be anchored in place in a relatively secure manner.

Briefly, the invention provides a shank for a hip joint prosthesis which has a blade, a neck and a collar which separates the neck from the blade. In accordance with the invention, the blade has a portion which widens conically from the distal end along a longitudinal median axis to an upper portion located between $\frac{2}{3}$ and $\frac{3}{4}$ of the height of the shank. In addition, the upper portion tapers to the collar with a medial narrow side of the upper portion extending on a steadily curved bend to the collar. The upper portion also tapers in the direction of the longitudinal median axis towards the collar.

The construction of the shank is such that the space requirement of the upper portion of the shank blade in a femur bone is decidedly reduced without impairment of the mechanical properties of the prosthesis, particularly the strength of the prosthesis, in the conical region of the shank blade or of the clamping effect and support of the conical portion in the femur bone.

In addition, the danger of shank bursting, as such may occur in the case of space-requiring implants with a shank cross-section which is rather square in the upper portion, is clearly reduced. Because of the two different curvatures of the upper end of a thigh bone (S-shaped as seen from the side), namely, the antetorsion of the femur neck (rotation forward) and the antecurvation of the shank (bending with the convexity forward), insertion of the prosthesis into the S-shaped curvature may be difficult. Under these conditions, tapering of the upper portion of the shank blade facilitates the insertion of the shank. Alternatively, for the same purpose, a transition may be provided between the conical part and the upper portion of the shank blade which ascends in a lateral direction.

The clamping effect and the support of the shank blade can be improved by additional measures. For example, the conical widening of the blade sides in the lower portion may be provided with a bead type central rib on each side with two grooves extending on opposite sides of each rib parallel to the medial and lateral sides of the blade. The blade may also be formed with a generally rectangular cross-section of such form and size so that the shank takes support on the cortical tissue of the femur via four rounded corners of the blade.

As is known, rotation movements of a leg in a hip are transmitted to the hip head and pelvis mainly by the gluteal muscles via the greater trochanter and the femur neck. If the joint is formed by a prosthesis, the torques must first be transmitted to the prosthesis shank before a rotation of the prosthesis head in an artificial pelvis will occur. However, these rotational movements make high demands on the stability of the implant. Thus, in the present case, the rotational stability of the shank can be improved if the lateral side of the tapered upper portion of the shank blade is widened to a trochanter wing at least approximately starting from the conically widening portion. In order to keep the surgical opening in the trochanter as small as possible, and thus, to leave a maximum of pre-existing spongiosa, the trochanter wing also tapers in a lateral direction towards the collar.

These and other objects and advantages of the invention will become more apparent from the following detailed description taken in conjunction with the accompanying drawings in which:

FIG. 1 illustrates an elevational view of a shank constructed in accordance with the invention;

FIG. 2 illustrates a side view of the shank of FIG. 1 from the lateral side;

FIG. 3 illustrates a view taken on line III—III of FIG. 1;

FIG. 4 illustrates a view taken on line IV—IV of FIG. 1;

FIG. 5 illustrates a view taken on line V—V of FIG. 1; and

FIG. 6 illustrates a view taken on line VI—VI of FIG. 1 of the shank in a femur.

Referring to FIG. 1, the shank for a hip joint prosthesis is provided with a blade 1 which extends along a longitudinal median axis 2, a neck 6 and a collar 4 which separates the neck 6 from the blade 1. As indicated, the blade 1 has a generally rectangular cross-section with a lower portion which widens conically from a distal end 13 symmetrically along the median axis 2 to an upper portion 18. At a function located between ⅝ and ¾ of the height of the shank.

The neck 6 carries a pin 7 which tapers conically outwardly along an axis 8 in order to receive a spherical joint head (not shown). The pin axis 8 intersects the median axis 2 of the blade 1 to form an angle 9 which essentially corresponds to the angle between the neck and axis of a femur of a natural hip joint, for example 49°.

The lower conical portion of the blade 1 has a bead type central rib 14 on each side to form the conical shape of the blade 1. In addition, a pair of grooves 15 are formed on opposite sides of each rib 14 in contiguous manner and in parallel relation to the medial and lateral sides of the blade 3 and 5 respectively. As shown in FIG. 2, each respective rib 14 tapers slightly in a widening manner from the distal end 13. The ribs 14 serve to enhance the clamping effect and support of the shank in a bone. Further, as shown in FIG. 6, the blade 1 is provided with suitable longitudinal and transverse dimensions as well as with four rounded corners 16 so that the blade 1 is supported on the shell of the cortical bone tissue 17, if possible, at all four corners 16.

Referring to FIGS. 1 and 2, the bead type central ribs 14 change over into the upper portion 18 of the blade 1 via a transition portion 19 which ascends i.e. is angled upwardly in a lateral direction as viewed in FIG. 1. Likewise, the grooves 15 terminate at the upper portion 18.

The upper portion 18 of the blade 1 is thinner than the lower portion in a plane (FIG. 2) perpendicular to the plane of the lateral width (FIG. 1) of the blade 1 and the collar 4. This thinner upper portion 18 may also taper toward the collar 4 as indicated in FIG. 2 or may have a constant thickness over the entire height. The upper portion 18 also has a medial narrow side 3 which extends on a steadily curved bend from the conical lower portion to the collar 4. On the upper portion 18 of the blade lateral narrow side 5 widens to a trochanter wing 20 which extends at least approximately from the conical lower portion, i.e. at the level of the transition 19. The wing 20 also tapers into the lateral direction outwardly, as viewed, from the median axis 2. The tapering of the wing 20 serves to keep the tissue resection in the trochanter which is necessary for inserting the wing 20 as small as possible. The portion of the wing which extends from the outermost lateral tip to the upper edge of the collar 4 extends in an arc and serves to improve the transmission of torques from the musculature via the prosthesis to the hip joint.

As shown in FIG. 1, the tapered upper portion 18 of the blade 1 has three bores 10, 11, 12 therein with the centers of the bores 10–12 defining a triangular array. The center of one bore 10 which is of a diameter somewhat greater than the other two bores 11, 12, lies on the longitudinal median axis 2 of the blade 1 while the bores 11, 12 have centers arranged on the pin axis 8 one behind the other at an exactly measured distance. In order to further establish the size and position of the triangular array enclosed by the bores 10, 11, 12, the perpendicular distance of the bore 10 to the axis 8 is a measured distance. These bores 10–12 serve to facilitate the comparison of x-ray pictures taken on the prosthesis from time to time. The distances between the bores may be selected at will; however, the distances should be as great as possible, without weakening the mechanical properties of the shank, for example the strength of the shank, since this would permit an improvement in the relative precision for the measured values on the x-ray pictures.

The invention thus provides a shank of blade type for a hip joint prosthesis which can be implanted in a femur in a more simplified manner than heretofore. In this regard, the provision of the transition 19 facilitates the insertion of the prosthesis in a correct position of the blade sides.

The invention further provides a shank of blade type which can be anchored without cement.

The invention further provides a blade type shank which can be fitted into place without altering the angular position of the planes of the shank blade relative to the transverse axis through a knee joint.

The shank also permits a resection plane on a femur neck to be made at a relatively high point.

What is claimed is:

1. A shank for a hip joint prosthesis, said shank having a blade, a neck and a collar separating said neck from said blade, said blade having a lower portion widening conically on all sides from a distal end along a longitudinal median axis to an upper portion at a junction located between ⅝ and ¾ of the height of said shank, said upper portion being thinner than said lower portion at said junction and in a plane perpendicular to the plane of the lateral width of said blade, said upper portion extending up to said collar with a median narrow side of said upper portion extending on a steadily curved bend to said collar.

2. A shank as set forth in claim 1 wherein said upper portion tapers in the direction of said longitudinal median axis towards said collar.

3. A shank as set forth in claim 1 wherein said upper portion has a lateral narrow side widened to a trochanter wing at least approximately starting from said conically widening portion.

4. A shank as set forth in claim 3 wherein said trochanter wing tapers into the lateral direction outwardly from said median axis.

5. A shank as set forth in claim 1 wherein said conically widened portion includes a bead-type central rib on each of at least two opposite sides and two grooves parallel to the medial and lateral sides of said blade in each said opposite side.

6. A shank as set forth in claim 1 wherein a transition portion between said conically widening portion and said upper portion is angled upwardly in a lateral direction.

7. A shank as set forth in claim 1 wherein said blade has a generally rectangular cross-section with four rounded corners.

8. A shank for a hip joint prosthesis, said shank having a blade, a neck and a collar separating said neck from said blade; said blade having a generally rectangular cross-section with a lower portion widening conically from a distal end along a longitudinal median axis to an upper portion at a junction located between ⅝ and ¾ of the height of said shank, said upper portion being thinner than said lower portion at said junction and in a plane perpendicular to the plane of the lateral width of said blade, said upper portion extending up to said collar with a medial narrow side of said upper portion extending on a steadily curved bend to said collar.

9. A shank as set forth in claim 8 wherein said blade has a transition portion between said lower portion and said upper portion angled upwardly in a lateral direction.

10. A shank as set forth in claim 9 wherein said lower portion has a central rib and a pair of parallel grooves on each of two opposite sides extending parallel to the medial and lateral sides of said blade.

11. A shank as set forth in claim 10 wherein said rib and said grooves on each side merge into said upper portion.

12. A shank as set forth in claim 10 wherein said upper portion has a lateral narrow side widened to a trochanter wing at least approximately starting from said conically widening portion.

* * * * *